United States Patent [19]

Wyatt

[11] 4,173,415
[45] Nov. 6, 1979

[54] APPARATUS AND PROCESS FOR RAPIDLY CHARACTERIZING AND DIFFERENTIATING LARGE ORGANIC CELLS

[75] Inventor: Philip J. Wyatt, Santa Barbara, Calif.

[73] Assignee: Science Spectrum, Inc., Santa Barbara, Calif.

[21] Appl. No.: 716,278

[22] Filed: Aug. 20, 1976

[51] Int. Cl.² ............................................. G01N 15/02
[52] U.S. Cl. .................................. 356/336; 250/564; 250/574; 356/343
[58] Field of Search .............. 356/102, 103, 104, 111; 250/564, 574

[56] References Cited

U.S. PATENT DOCUMENTS

| 3,624,835 | 11/1971 | Wyatt | 356/103 |
| 3,834,818 | 9/1974 | Meric | 356/102 |

OTHER PUBLICATIONS

Wyatt, "Differential Light Scattering: a Physical Method for Identifying Living Bacterial Cells," *Applied Optics*, vol. 7, pp. 1879-1896, Oct. 1968.
Bonner et al., "Fluorescence Activated Cell Sorting," *Review of Scientific Instruments*, vol. 43, pp. 404-409, Mar. 1972.

*Primary Examiner*—John K. Corbin
*Assistant Examiner*—Matthew W. Koren
*Attorney, Agent, or Firm*—Spensley, Horn, & Lubitz

[57] ABSTRACT

To characterize and differentiate large organic cells rapidly, individual particles are illuminated with monochromatic radiation of a wave length comparable to the size of the cell, producing a differential light scattering pattern about the illuminated cell. The pattern is sensed, preferably in the disclosed apparatus, by an array of detectors, and the sensed pattern employed as an identification and characterization of the cell. The pattern may be analyzed, or selected portions of the pattern employed, to differentiate cells embodying different features. The apparatus and process is especially useful for rapid identification and differentiation of leucocytes and other types of mammalian cells, the radiation for such analyses preferably being infrared radiation. A preferred structure for individually illuminating such cells with radiation and for sensing their differential light scattering pattern is disclosed.

33 Claims, 12 Drawing Figures

FIG. 1.
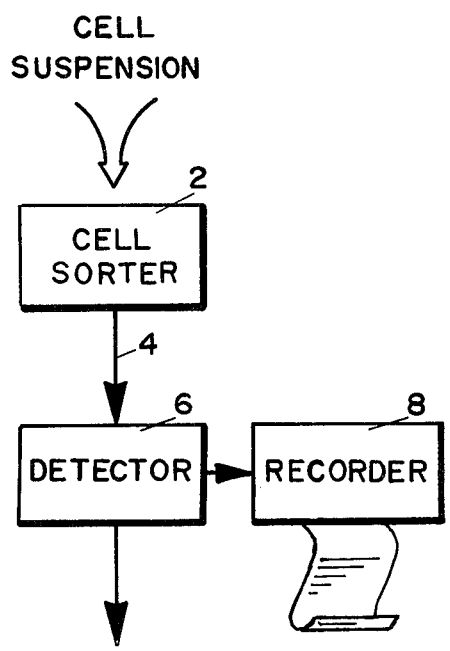
FIG. 2.
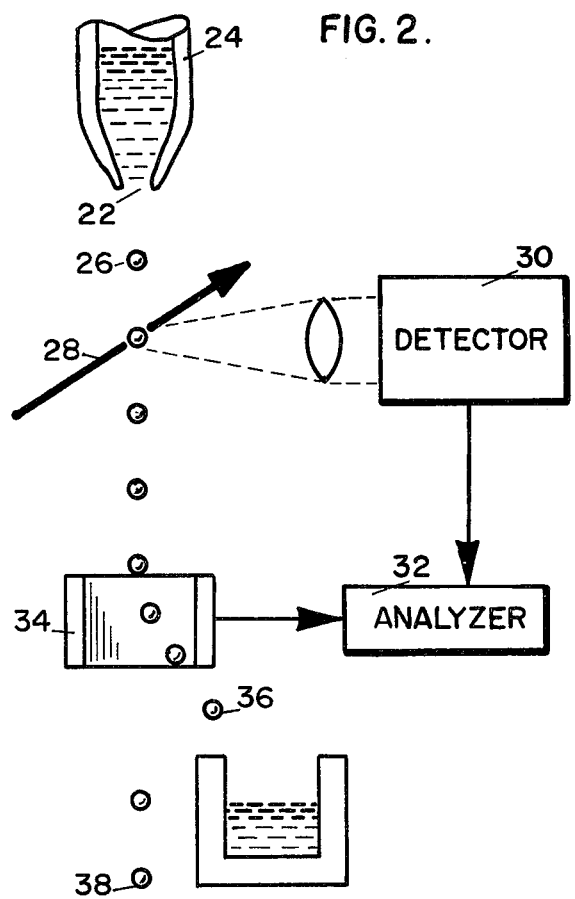
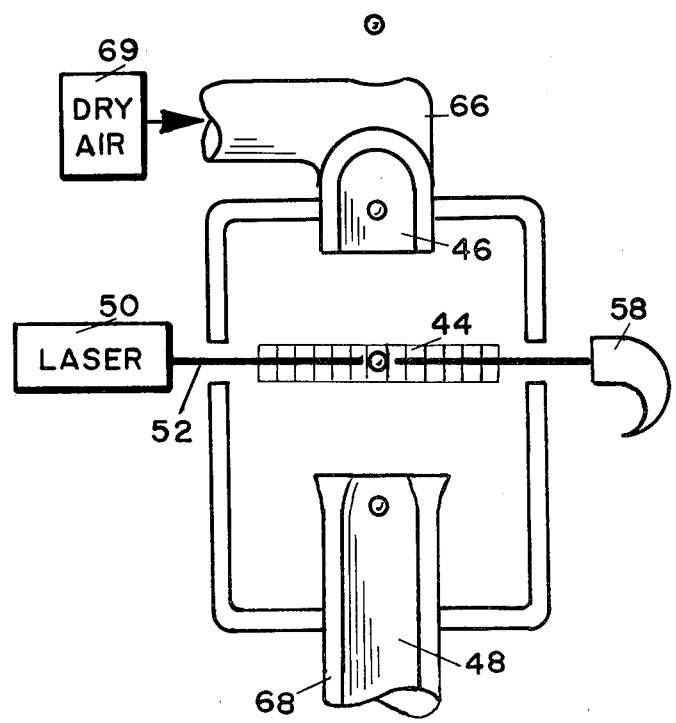

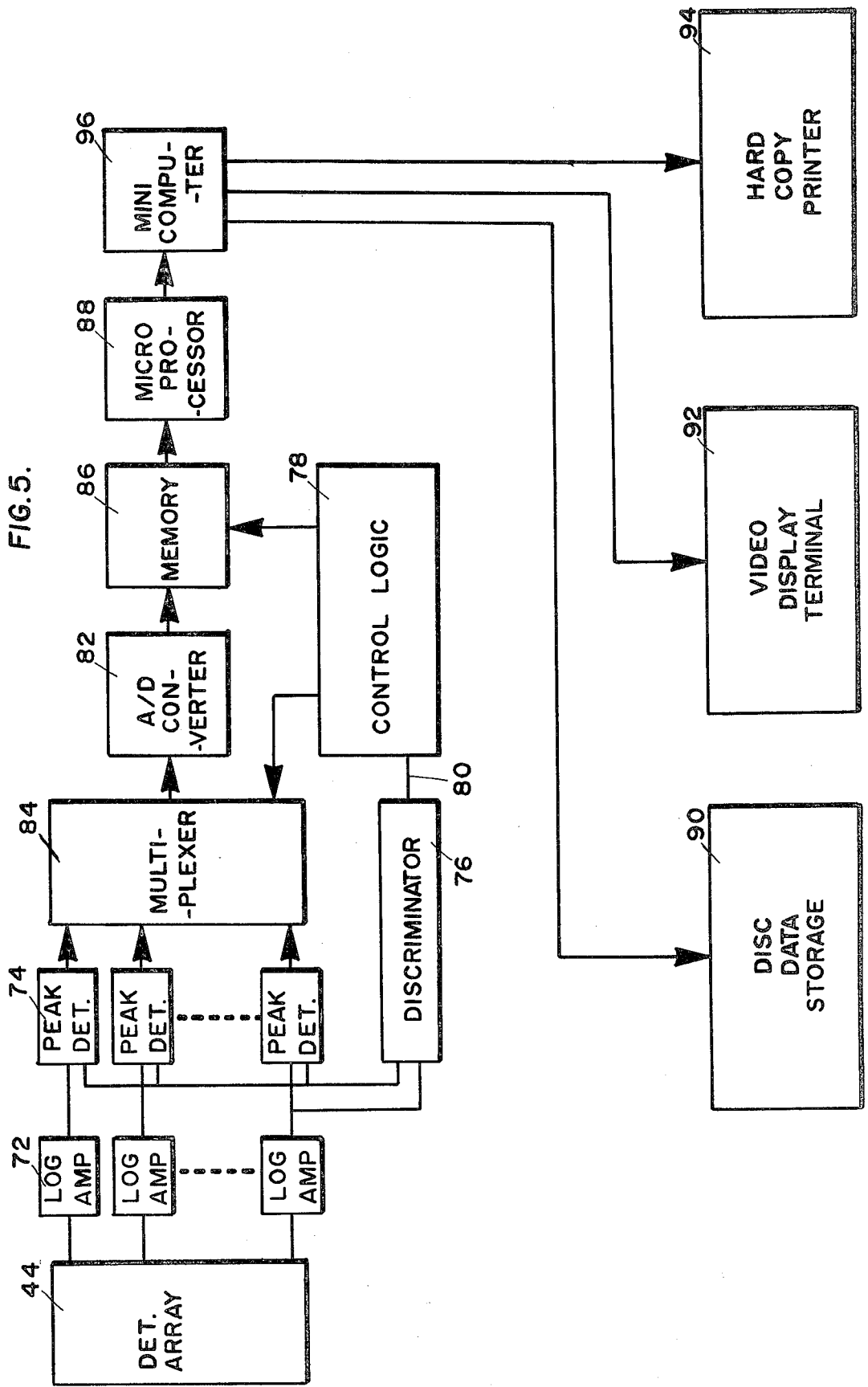

APPARATUS AND PROCESS FOR RAPIDLY CHARACTERIZING AND DIFFERENTIATING LARGE ORGANIC CELLS

PRIOR RELATED APPLICATION AND PATENTS

The present invention is directed to the use of differential light scattering to rapidly characterize and differentiate large organic cells, particularly leucocytes and other types of mammalian cells. To this end, a process, an apparatus, and a preferred sensor structure is disclosed, and various modifications thereof are suggested. Prior related patents and an application assigned to the assignee of this application include:

U.S. Pat. No.: 3,624,835
  Title: Microparticle Analyzer Employing a Spherical Detector Array
  Inventor: Philip J. Wyatt
  Date of Issue: Nov. 30, 1971

U.S. Pat. No.: 3,770,351
  Title: Optical Analyzer for Microparticles
  Inventor: Philip J. Wyatt
  Date of Issue: Nov. 6, 1973

U.S. Pat. No.: 3,730,842
  Title: Process for Determining Bacterial Drug Sensitivity
  Inventor: Philip J. Wyatt, et al.
  Date of Issue: May 1, 1973

U.S. Pat. No.: 3,754,830
  Title: Scattering Cell Employing Electrostatic Means for Supporting a Particle
  Inventor: D. T. Phillips, et al.
  Date of Issue: Aug. 28, 1973

U.S. Pat. No.: 3,928,140
  Title: Apparatus and Process for Testing Microparticle Response to its Environment
  Inventor: Philip J. Wyatt, et al.
  Date of Issue: Dec. 23, 1975

Co-pending application Ser. No. 139,366, now abandoned
  Title: Light Scattering Photometer Recorder Unit
  Inventor: H. H. Brooks, et al.
  Date of Filing: May 3, 1971

BACKGROUND

For many years, there has been a need for a way to identify and differentiate large organic particles rapidly, particularly leucocytes and other types of mammalian cells. To this end, numerous physical techniques have been proposed, and machines and processes have been developed that employ these techniques. Such techniques include chemical staining methods, chromatographic analytical methods and physical methods such as automated microscopic examination systems. All of these techniques are quite limited in their capabilities, in the population of cells that they can analyze, and in their analytical speed. More importantly, many of the techniques have been shown to be of questionable accuracy.

The present invention is directed to an apparatus and process for rapidly identifying, characterizing and differentiating cells, particularly leucocytes and other mammalian cells. It employs an analytical technique known as differential light scattering, a technique which has been shown to be capable of rapid and accurate analysis of microparticles.

The terms "identifying", "characterizing" and "differentiating" cells are used in describing the usefulness of the invention. "Identifying" means to determine what the cell is, e.g. a polymorphonuclear leucocyte, while "characterizing" describes its physical features, such as size, shape, and dielectric structure, and "differentiating" separates or distinguishes different types of cells, such as sickling red blood cells from normal red blood cells, or normal lymphocytes from abnormal lymphocytes with inclusions, or cancerous squamous cells from their normal counterparts, etc.

Various systems have been described in the published literature that employ differential light scattering techniques to analyze mammalian cell systems. Such publications include "A Flow System Multi-Angle Light-Scattering Instrument For Cell Characterization" by G. C. Salzman and others, this article appearing in the *Journal of Clinical Chemistry*, Vol. 21, No. 9, pgs. 1297 to 1304 (1975), and "Cell Classification by Laser Light Scattering: Identification and Separation of Unstained Leucocytes" by G. C. Salzman and others which appeared in *Acta Cytologica*, Vol. 19, No. 4, pgs. 374 through 377 (1975). These articles describe systems which employ a monochromatic light beam to illuminate water suspended mammalian cells, the resulting differential light scattering pattern being quite complex. For that reason, an empirical approach was employed to determine which discrete areas of the overall differential light scattering pattern could be employed to isolate a specimen population of certain characteristics from populations of other characteristics. Obviously, such empirical approaches are quite limited, both in their ability to handle various cell populations and in their ability to produce meaningful results.

SUMMARY OF THE INVENTION

The present invention provides an apparatus and process for rapidly characterizing and differentiating cells, particularly leucocytes and other types of mammalian cells. It employs a beam of polarized, monochromatic illumination that is of a wavelength which is approximately equal to the size of the cells of interest in the cell population to be analyzed. Individual cells of that population are illuminated by the beam, the cells of interest producing differential light scattering (DLS) patterns that exhibit resonant scattering characteristics having relatively broad maxima and minima, i.e., each maxima and minima will extend over an angular range usually on the order of 10 to 30 degrees. These patterns are neither so simple in shape nor so complex in detail that little or no useful information can be gleaned from them. Rather, because they are produced by a resonant scattering system, they embody sufficient significant features to characterize accurately each individually illuminated scatterer, particularly such physical features as its size, shape, and dielectric structure, permitting the scatterer to be accurately and unambigously identified and differentiated.

The practical application of light scattering phenomena to the identification, characterization, and differentiation of large organic particles begins with a conventional liquid suspension of such cells. This suspension is aerosolized by the apparatus, and in the preferred process, droplets are produced, some of which may contain a cell. These droplets are examined and those which contain a cell are separated from the other droplets, then the liquid surrounding each cell is evaporated to result in a stream of free, airborne cells. Each of these separated cells is illuminated in sequence with a beam of polarized, monochromatic radiation of a wavelength approximately equal to the average size of the cells being examined, such as a wavelength in the infrared region for a suspension of mammalian cells. The illumination scattered by each cell is detected at a sufficient number of angular locations about the cell to provide a differential light scattering pattern characteristic of the physical properties of the cell.

These successive DLS patterns are recorded and analyzed to identify, characterize, and differentiate the cells. As an example of such an analysis, the patterns produced by individual cells may be processed to determine certain intensity ratios, such as the ratios of the first peak intensity to the intensities of subsequent peaks, and then cells with similar numbers of peaks in their differential light scattering patterns may be sorted in a multi-dimensional analysis based upon these ratios to group cells of similar features. By means of such an analysis of various types of known cells, unknown cells may be identified with known cell types. The detectors used to determine the differential light scattering paterns need not subtend uniform solid angles nor be normalized to a uniform dark current; by employing the same system throughout the analysis, such differences as these will not affect the results. Other variations in the disclosed apparatus and process are set forth in the detailed description and noted in the claims.

BRIEF DESCRIPTION OF THE DRAWINGS

Although there are many possible types of instrumentation configurations that will suitably measure, record, and analyze DLS patterns from large particles, in accordance with the teachings herein set forth, there are certain basic elements that are required for a practical system. These include a means to handle cells and introduce them one at a time into a laser beam. The laser itself is preferably a plane polarized carbon dioxide infrared source operating at about 10.6 $\mu$m, however, other sources producing a suitable wavelength may be used. The laser should preferably be coplanar with the line of sight of an array of 10 to 50 individual elements. Ideally, the number of detector elements required in the array, N, is given in terms of the vacuum wavelength, $\lambda_o$, the largest present particle diameter, D, the refractive index, $n_o$, of the medium in which the measurement is made, and the angular range spanned by the array $\theta$, by the simple relation $N \approx [2\pi D n_o / \lambda_o + 4] \theta / 180°$. For mammalian cells illuminated with infrared radiation of 10.6 $\mu$m, this number lies between about 10 and 50. Although the array elements lie preferably on an arc subtending 100° or more, a sufficient DLS pattern may be obtained from other element configurations, e.g. wherein the elements are not on an arc, are not equidistant from the scattering particle, the angular range subtended is even less than 100°, or the detectors are not equidistantly spaced.

Such a preferred structure and system is illustrated in the accompanying drawings, in which:

FIG. 1 is a schematic diagram of the preferred apparatus;

FIG. 2 is a view in vertical cross-section of the cell handling portion of the preferred apparatus;

FIG. 5 is a schematic diagram of the analytical system for the preferred apparatus;

DETAILED DESCRIPTION OF THE INVENTION

Introduction

Figure 3:
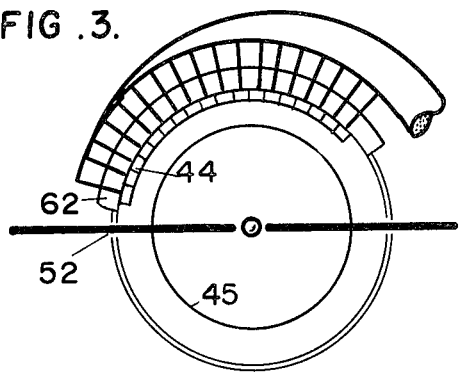
FIG. 3 is a view in horizontal cross-section of the detector housing showing the detector array.

Central to an understanding of this invention is an understanding of differential light scattering. While the basic concept of differential light scattering is explained in many patents and publications, especially those by the present inventor, briefly it employs a polarized monochromatic radiation source to illuminate one or more particles, the particles scattering the illumination in a way characteristic of their physical features, features such as size, shape and dielectric structure. This pattern of scattered illumination may be sensed by rotating a collimated detector about the scatterer or using an array of fixed detectors; the measured intensity may be recorded as a function of detector angle to plot a differential light scattering pattern.

Such differential light scattering patterns may contain a great deal of information about the scatterer, or they may yield little or no information about the scatterer. For example, if the size of the particle is quite small in relation to the wavelength of the illuminating beam, little or no variation will be exhibited in the intensity of the scattered radiation as a function of angle about the particle. On the other hand, if the size of the particle is quite large in relation to the wavelength of the illuminating beam, a great many maxima and minima will be exhibited in the scattering pattern. Interpreting such patterns to extract salient particle characteristics is a major task.

This task may be simplified significantly by adjusting the wavelength of the illuminating monochromatic light source to be approximately equal to the overall size of the illuminated particle. When such approximate equality exists, i.e., the particles are in the "resonance" region the resultant differential light scattering pattern will exhibit maxima and minima, yet it will not be so complex that many features directly correlated to particle structure are hopelessly lost in the detail.

The use of resonance scattering techniques is quite significant. The differential light scattering patterns are complex functions of the particle size, shape, orientation, and structure, as well as the polarization and wavelength of the incident radiation. The most critical scattering parameter is the normalized size; i.e.

$$\rho = (\pi D n_o / \lambda_o) = ka \tag{1}$$

where "a" is the mean particle radius, $D(=2a)$ the corresponding diameter, $\lambda_o$ the vacuum wavelength of the incident radiation, and $n_o$ the refractive index of the medium surrounding the particle. Variation of the size parameter, $\rho$, most affects the corresponding differential light scattering pattern, but size itself is certainly one of the least important, and most ambiguous, parameters for distinguishing anomalous cells from normal cells, or one type of leucocyte from another, or one type of pollen from another. In addition, the size distributions invariably overlap. As $\rho$ becomes very large, the differential light scattering patterns are overwhelmed by the additional peaks which are of little analytical importance.

If the DLS pattern is to be recorded by an array of N detector elements, it can be shown that the optimal number of such detectors spanning the complete angular range from 0° to 180° is given simply by $$N \approx 2\rho + 4 \qquad (2)$$

In other words, from the intensity data recorded at the N suitably spaced locations spanning the entire 180° range, the DLS patterns may be very accurately interpolated between all these locations. If the angular range of interest be less than this 180°, then the number of detector elements may also be suitably reduced approximately by the ratio of the range spanned to 180°. Now for any particular measurement using such an array to sense the DLS pattern, the largest number of detector elements required is dictated entirely by the size of the largest particle of interest to be measured. Thus $\overline{N}$ should always be chosen to be about $2\rho_{max}+4$, where $\rho_{max}$ corresponds to the normalized size of the largest particle of interest expected in the suspension to be studied. For an airborne squamous cell of mean diameter 60 μm illuminated by an infrared wavelength of 10.6 μm, the optimum number of detector elements woulld be about $$(2\pi 60/10.6) + 4 \approx 40 \qquad (3)$$

At large scattering angles, internal structure will play a major role in determining the variations of differential light scattering features. Indeed, this long-known fact, pointed out by the present inventor in 1968 in Vol. 7 of *Applied Optics* pgs. 1879 to 1896, has been the basis for the extensive differential light scattering programs being conducted at the Los Alamos Scientific Laboratory. By use of larger angle differential light scattering measurements, the LASL group has hoped to be able to differentiate among similar types of mammalian cells. Their measurements have been made using He-Ne lasers operating at a visible wavelength of 632.8 nm. Such wavelengths are extremely small compared to the mean dimensions of the squamous cells examined. Although some successes have been reported, the ultimate limit of such measurements using so short a wavelength may well have been reached already. The reason for this is straightforward. At larger scattering angles, the differential light scattering patterns for such large values of $\rho$ are intimately dependent on $\rho$ through the parameter $$\xi = \bar{n}\rho p \quad (4)$$

where $\bar{n}$ is the mean refractive index of the scattering particle divided by $n_o$. Since different types of mammalian cells would be expected to have slightly different $\bar{n}$ values, though most importantly they fall into different size domains, some separation based on $n\rho$ measurements would be expected. The reported LASL differentiations using "cluster algorithms" are fortuitous, but will be hard-pressed to distinguish between cells with comparable $\bar{n}\rho$ values. Although they were apparently aware of the importance of using longer wavelength radiation, the problems associated with infrared radiation could well have been discouraging.

The present invention is based upon the realization that differentiation and characterization of mammalian cells and other large organic particles by differential light scattering techniques will be practical if, and only if, the measurements are performed using infrared radiation, for at these resonance wavelengths the size of the particles being illuminated is comparable to the wavelength of the illuminating radiation. This may be confirmed by considering first the other two size regimes, the regimes in which particles are very small compared to the illuminating radiation and in which the particles are very large compared to the illuminating radiation.

In the former case using, say, microwave radiation, it can be shown that there will be no angular variation in the scattered intensity. Accordingly, the intensity measurement need only be made at a single angle, any angle. The absolute scattered intensity from a single "small" particle, if such could be practically measured, cannot be used to classify or separate particles, since such a quantity is ambiguous; i.e., no single intensity value may be associated with a particular class of mammalian cell. Slightly different normalized sizes, $\rho$, are easily compensated by variations in mean relative refractive index, $\bar{n}$ and vice versa. Furthermore, any structural or shape differences between different classes of cells will have no single-valued effect upon the scattered intensity and thus these differences also will be undetectable.

In the latter case, using, say, visible light, when the size of the particle is very large compared to the wavelength of the illuminating radiation, the differential light scattering pattern will embody more scattering detail than is needed to account for the particle's important structural features. An example of such patterns and the immense detail they present is illustrated by the patterns incorporated in the article "Scattering by Individual Transparent Spheres" by H. H. Blau and others which appeared in *Applied Optics,* Vol. 9, pg. 2522 et seq. (1970). The plethora of data for each measurement presented in that article has resulted from an exceedingly simple scattering system: a spherical droplet of a uniform dialectric structure illuminated by polarized monochromatic radiation of a wavelength approximately one onehundredth the size of the particle.

The present invention is directed to the rapid identification, differentiation, and characterization of cells that are quite large compared to the wavelength of visible light, particularly various types of mammalian cells. These cells often incorporate a membrane of one dielectric structure surrounding an interior of another dielectric structure which may include various particles and structural anomalies of still other dielectric structures. The shape and size of these various structures often are quite non-spherical, some for example being platelet shaped. Should visible illumination, i.e. radiation whose wavelength is very small compared to the mean diameter of these particles, be employed to obtain differential light scattering patterns for such particles, not only would an enormous number of maxima and minima be present in such patterns, but also, even minute changes in any of these structural characteristics will result in enormous changes in the scattering patterns. These considerations illustrate the near futility of attempting to use such complex differential light scattering patterns to distinguish between particles of different composition. Yet many have proposed and employ just such analyses.

As has been noted, this invention is directed to an apparatus and process for rapidly identifying and differentiating large organic cells, especially mammalian cells. Such cells typically range from a few micrometers in diameter to no more than a few tens of micrometers in diameter. These cells include leucoytes, erythrocyctes and squamous cells. If such individual cells are illuminated with a beam of polarized, monochromatic radiation of a wavelength on the order of, say, 10 micrometers, then broad maxima and minima will be exhibited in the differential light scattering pattern produced by this system. This relationship, one in which the size of the particles are in the so-called resonance region, produces patterns having features which are far more easily correlated to structural differences of the scatterer. Modest changes in the particles' average features will result in significant changes in the pattern in certain angular ranges, yet for particles of comparable size, the overall patterns will be quite comparable in shape. Moreover, while such patterns will include sufficient detail to permit accurate characterization and differentiation of various particles, they do not include so great an amount of detail as to mask or impede the accurate mathematical interpretation of the physical features of the scatterer. This realization, that the illuminated particles and the wavelength of the illuminated beam should be of roughly comparable size, makes practical the rapid and unambiguous characterization and differentiation of mammalian cells and other large organic cells. Also, it gives rise to a relatively simple, yet eminently practical, apparatus and process for performing such analyses.

The necessity of this relationship dictates use of an infrared laser for the analysis of mammalian cell systems. Mammalian cells incorporate, and usually are surrounded by, water-like fluids. This presents a significant difficulty. The absorption coefficients of water in the infrared region are very large. Thus, the water normally present in and around such cells will play a major role in any resonance differential light scattering measurement from mammalian cells. When water suspensions of cells are illuminated by infrared radiation, attenuations of the illuminating beam on the order of 90% or greater would be expected within distances as small as the dimension of the cells. Furthermore, such attenuation also would affect the radiation scattered by the cells by severely distorting and attenuating the scattered waves emerging from the suspending liquid.

It is not surprising, therefore, that those skilled in the art of differential light scattering measurements and infrared radiation apparently long ago dismissed the possibility of making meaningful DLS measurements from such large organic particles at these wavelengths. Attenuation by a water sheath or even the water within airborne cells themselves appears superficially to all so skilled to preclude the practical application in infrared radiation. Recognizing that the scattering of radiation by objects in the resonance region is not generally governed by the geometrical optics attenuation relations, the expected scattering properties of heavily water-laden particles in the infrared resonance region have been determined and are described later in this disclosure. They demonstrate conclusively that such particles may be distinguished by their DLS patterns provided that they are surrounded by a gas such as air that does not strongly absorb infrared. Because of this, it is preferred to perform the scattering measurement of a cell in a gaseous environment. While air is employed as the gas in the preferred structure now to be described, it should be understood that any of a variety of other gases could be employed if desired; or the analysis even could proceed in a vacuum provided the particles of interest maintained their structure in such an environment; or if an infrared transparant fluid were found, the measurements could even be performed therein; or if only a relatively thin layer of water coated the cells, the measurements could be performed with no problems.

SUMMARY OF THE PREFERRED EMBODIMENT

As noted, the practical application of the resonance scattering phenomena to large organic particles such as mammalian cells or pollen particles requires the use of polarized infrared radiation at a wavelength of about 10 $\mu m$. In summary, the cells or particles are first aerosolized, then transported through a detector array by means of a laminar flow of dry gas. The detector array, consisting of $N \simeq 2\rho_{max}+4$ discrete detector elements, preferably subtends an angle of about 100° of the DLS pattern produced by the individual particle as it passes through a collimated laser beam, the beam preferably being coplanar and at right angles to the array elements. Certain detectors, may have to be cryogenically cooled and insulated from the dry gas stream by means of an insulating cylinder including windows made of an infrared transparent substance such as germanium.

As a particle passes through the laser beam it produces a pulsed spherical wave of duration D/V, where D is the beam diameter and V is the particle/stream velocity. The individual detector elements convert the pulse they receive into an electrical signal that is amplified and stored, preferably in digital form after conversion, in a computer memory or on a tape. These $N \simeq 2\rho_{max}+4$ stored signals may be used to reconstruct the continuous DLS pattern from the particle by interpolation procedures using Tchebyshev polynomials, or related procedures, or the stored signals may be used directly. The angular spacing of the individual elements may be equidistant, though for certain types of subsequent analyses it may be preferable to space them according to the locations of the N roots of the Tchebyshev polynomial, $T_N(X)$, as will be apparent from this disclosure to those skilled in such analyses, where N is the number of detector elements, $X=[\theta-(\theta_2+\theta_1)/2]/[(\theta_2+\theta_1)/2]$, and $\theta_1<\theta_2$ define the angular range over which the DLS pattern is to be recorded.

Once the DLS patterns, or sets of array data points from which such patterns may be reconstructed, have been stored, these patterns may be analyzed by means of various algorithms so that each particle may be identified or otherwise suitably characterized. Most practical algorithms have been found to be based on a characterization procedure that first groups particles into sets of equal size. The average size of the particles may be sufficiently estimated by counting the number of DLS peaks between two angular limits or by determining the angular position of a specific peak with respect to the forward direction. Since such a deduced size parameter is not a conclusive means for identification or differentiation, its exact value is unimportant so long as particles of the same effective size are all compared with one another. Having established that all particles in a given set are effectively of the same size, e.g. have the same number of peaks between two angular limits, the particles may be structurally and physically distinguished from one another by various sorting algorithms. These algorithms may characterize DLS patterns by comparing various ratios of a given DLS pattern. For example, the ratios of the heights of the DLS peaks in a given angular range to the height of the first peak in that range are a useful set of differentiation parameters, as will be detailed subsequently. Other ratios would include various peak-to-valley values as well as ratios involving functionally more complex terms based on the various peak heights and valley depths present. All such ratios are functions of the scattering particle's dielectric structure and may be used therefore to characterize each particle. Once such ratio characterizations have been achieved for each of the size groups of particles present, these may be further analyzed by means of a stored catalogue of such ratios contained in the computer memory of the system's analytic processor. The distribution of such scattering ratios as a function of particle size set represents another important means for identifying, characterizing and differentiating particles.

DESCRIPTION OF A PREFERRED APPARATUS

As shown in FIG. 1, a schematic illustration of the various means or elements of a preferred apparatus, a suspension of cells to be analyzed is supplied to a cell sorter 2 similar in construction to that described by W. A. Bonner, et al. in "Fluorescence activated cell sorting" appearing in Rev. Sci. Instruments, 43, pg. 404 et. seq. (1972). This cell sorter, shown in more detail in FIG. 2, separates the liquid suspension of cells into a series of discrete droplets, the separate droplets being of a size small enough to contain no more than one mammalian cell or particle. As set forth in the noted description, these droplets are electrostatically charged, illuminated by a light beam to determine if they contain a particle, then sorted by electrostatic deflection to produce a droplet stream containing only droplets that incorporate mammalian cells. This droplet stream 4 is supplied to a detector system 6, also illustrated in FIG. 2, that illuminates each droplet with a polarized monochromatic beam, preferably an infrared laser of 10.6 micrometers wavelength. The illumination scattered by each cell in succession is measured by a sensor system, preferably an array of sensors, incorporated in the detector 6. The output electrical signals of each detector then may be transmitted to and stored in a recorder 8 such as a magnetic tape recorder. The stored data then may be analyzed by a computer analyzer. After sufficient particles have been analyzed, the computer may summarize the results and provide an output in tape, disc, or hard copy form, as will be described subsequently.

FIG. 2 illustrates in more detail the sorter and detector portions of the preferred apparatus. As described in the article by W. A. Bonner, et al., the liquid suspension of cells passes from an orifice 22 in tube 24 producing a series of droplets 26, each droplet being charged by an ionization source. These discrete droplets are illuminated by a beam 28, the scattered intensity from each droplet being sensed by a detector 30, amplified, and transmitted to an analyzer 32 which controls and supplies an electric potential to a set of electrostatic deflection plates 34. The stream of droplets passes between the plates of this electrostatic deflection system. As described in the article by Bonner, et al., the scattering produced by each successive droplet and measured by the detector 30 is analyzed to determine the presence or absence of a cell in that droplet, the analyzer energizing the set of deflection plates to electrostatically deflect from the stream those droplets 36 which do not contain a cell. The remaining droplets 38 which do contain a cell or particle pass to the detector system.

The detector system incorporates in a housing or scattering chamber 42 an array of sensors 44, an inlet 46, and an exhaust opening 48. A radiation source 50, preferably a laser, produces a beam of monochromatic, preferably plane polarized, infrared radiation 52. This beam passes into the housing 42 through an opening 54 and from the housing through an opening 56, thereafter passing into a Rayleigh horn or light trap 58. Preferably, the axis along which the beam passes lies in the plane of detector sensor array 44, and is orthogonal to the axis along which the stream of droplets pass, although this relationship is not essential to the operation of the apparatus as is noted subsequently. The detector array preferably is a liquid nitrogen cooled multi-element mercury-cadmium-telluride [Hg Cd (Te)] array such as produced by Honeywell Corporation Radiation Center, although other suitable arrays are produced by other groups such as Arthur D. Little & Co. and the Santa Barbara Research Center, a subsidiary of the Hughes Aircraft Corporation. Such detectors have very high detectivities making them most suitable for this measurement. However, the requirement to cool them cyrogenically may be inconvenient or undesirable in some applications. Accordingly, pyroelectric detectors which may be operated at normal room temperatures are also most suitable for measurements in the vicinity of 10 $\mu$m. Although the detectivities of such detectors are less than those of the cooled Hg-Cd(Te) type by a factor of about 100, the availability of almost unlimited power radiation sources, such as $CO_2$ lasers insures a more than adequate scattered signal. Pyroelectric detectors are also considerably less expensive than their Hg-Cd(Te) counterparts, thereby promising greatly reduced fabrication and operating costs. A collection of papers by Honeywell Corporation staff is particularly appropriate. This "Compendium of Honeywell Publications on Pyroelectric Detectors and Materials" is available from the Honeywell Corporation Radiation Center in Lexington, MA. It includes many related papers, both published and unpublished, pertinent to the preferred sensor array, papers such as:

S. T. Liu, J. D. Heaps and O. N. Tufte, "The pyroelectric properties of the lanthanum-doped ferroelectric PLZT ceramics," Ferroelectrics 3, pgs. 281 through 285 (1972), and A. van der Ziel and S. T. Liu, "Noise sources in pyroelectric radiation detectors," Physica 61, pgs. 589 through 593 (1972).

Preferably, the individual elements of the array are spaced from one another about 2 mm, 10 to 50 discrete elements being distributed over an arc of approximately 100° extending from a scattering angle of 30° to a scattering angle of 130°. If the elements are Hg-Cd(Te) detectors, such an array must be cryogenically cooled. To this end, a source of liquid nitrogen at cryogenic temperature [about 77° K. for a Hg Cd (Te) detector array] is supplied to a jacket 62 (FIG. 3) incorporated in housing 42 and surrounding the detector array 44. Preferably, the inner surface of the cylinder about which the array is spaced has a radius of about 1 centimeter. If the detectors are to be cryogenically cooled, they must be isolated from the air environment by means of a vacuum between the detectors and the flowing air stream. This is most readily achieved by means of a concentric inner structure, 64, the volume between the array 44 and the innermost well 45 being evacuated. This inner structure includes suitable windows made of germanium or any other infrared transparent substance.

The liquid volume of the droplets about the cells is evaporating as the cells pass from the cell sorter in and through the detector. Preferably the humidity of the transporting air stream is adjusted so that the liquid enveloping the cell in the droplet is just evaporated during transit of the cell from the sorter to the detector providing a free airborne cell for illumination in the detector region. Thus, the atmosphere flowing along with the cells will tend to be rather humid. Should this humid atmosphere encounter cryogenic temperatures, or even be cooled to any significant degree, condensation may occur. Such condensation would significantly affect the light scattering measurement. To avoid such problems, it is preferred both to minimize the volume of the atmosphere flowing into the detector with the stream of cells and also to surround this atmosphere and stream of cells with an insulating sheath of dry gas. Also, as noted, the aerosolization process should be separated sufficiently from the detector to permit all accreted water to evaporate yet not dehydrate the cells. Ideally, the liquid surrounding each cell shall have evaporated just before the cell enters the detector array, yet no liquid internal to the cell have had an opportunity to transpire through the cell membrane. The sheath of dry air is provided from a source of dry air 69 through a collar 66 which introduces it into the detector as a laminar flowing column about the stream of cells, this column of dry air isolating the stream of cells from the infrared window 64. The column of dry gas and the stream of cells it surrounds is exhausted through opening 48 in the housing, passing through a conduit 68 at negative pressure to a receptacle (not shown).

As best shown in FIG. 3, when each individual cell passes through the beam of radiation 52 it scatters that radiation, some of the scattering being intercepted by each discrete detector in the detector or sensor array 44. The resultant discrete electrical signals produced by each detector in the array are transmitted through the cable 8 to a subsequent electronic analysis and recording system.

Especially when considering mammalian cells, should the data include significant structural and surface differences in addition to size and refractive index variations, it will present an analytical interpretation task well beyond the means of current technology. Such easily can be the case when large particles are illuminated with visible light. Most importantly, the plethora of detail in such differential light scattering patterns derived using visible light appears to bear no simple, interpretable relation to the amount of physical data that may be deduced from them. Extracting the salient particle characteristic from such patterns, if possible, presents at best an immense task.

It might be argued, however, that one could record the differential light scattering patterns with much less angular resolution and thereby minimize the abundance of data relative to the physical parameters involved. However, as is revealed by an examination of such patterns as presented, for example, in the *Applied Optics* paper by Blau, et al., even the envelopes of such differential light scattering patterns change significantly for miniscule changes in the scattering particle's structure. Thus, decreasing the angular resolution will not in itself result in a satisfactory improvement of the parameter deduction problem.

Illustrated in FIG. 4 are computer-generated differential light scattering patterns for cells with a high water content illuminated by a vertically polarized (electric vector in a plane orthogonal to the plane viewed by the sensors) beam of monochromatic radiation having a wavelength of 10.6 micrometers. The cells in FIG. 4*a* have a radius of 10 micrometers, and the cells in FIG. 4*b* have a radius of 20 micrometers. The former size would be similar to leucocytes, whereas the latter would begin to approach that of squamous cells. In these examples, four different compositions have been chosen, compositions that would correspond to slightly different amounts of protein in the particles. Since the presence of additional protein will increase only the real part of the refractive index of the particle, the four examples selected exhibit only slight changes in this real part of their average refractive indices; to wit:

A: $n=1.176+i0.084$ (This is the approximate value of the refractive index of pure water at 10.6 $\mu$m; i.e. an 'empty' droplet)

B: $n=1.20+i0.084$

C: $n=1.25+i0.084$

D: $n=1.30+i0.084$

The respective curves in each figure are in the order indicated by the respective letters. FIGS. 4*c* and *d* illustrate patterns corresponding to particles identical to those yielding FIGS. 4*a* and *b*, respectively, except that the patterns of FIGS. 4*c* and *d* result from horizontal polarization (electric vector in a plane coincident with the plane viewed by the detectors) of the illuminating infrared radiation.

As this data illustrates, relatively simple structural changes in the scatterer produce relatively simple changes in the differential light scattering pattern. For the smaller particles, the horizontally polarized scattered intensity at around 40° (FIG. 4*c*) relative to the intensity at 50° provides a simple yet excellent measure of the physical differences of the postulated cells. Similar simple and obvious differences for the larger cells are shown in FIG. 4*d*. Accordingly, while differential light scattering patterns produced by such cells when illuminated with shorter wavelengths of visible radiation are extremely complex and yield a plethora of data far in excess of the number of physical parameters involved, the corresponding patterns obtained at longer infrared wavelengths in which the particles and illuminating radiation are in the resonance region result in data that is far easier to understand and to interpret. This permits particles to be identified, differentiated, characterized and analyzed accurately with relatively simple, readily available computerized equipment.

It should be noted particularly that the particles producing the patterns illustrated in FIGS. 4*a*–*d* have refractive indices close to that of water in the infrared, i.e., have a high water content, and are therefore highly absorbing in the infared. Nevertheless, their scattering patterns show distinctive differences for relatively small though significant composition changes. Because of the large imaginary part of the refractive index, such differences would not generally be expected. Therefore, those traditionally skilled-in-the-art would avoid using infrared radiation and not even attempt to check their intuitively wrong expectations by means of analyses such as these.

A preferred analytical system is shown in FIG. 5. As previously explained, when each cell of the cell suspension passes through the cell sorter, it results in a differential light scattering pattern being impressed upon and sensed by the detector array 44. In one embodiment of the system, shown in FIG. 1, these successive differential light scattering patterns, or more precisely the successive intensity measurements produced by the array of detectors, may be recorded by a recorder 8, such as a magnetic tape recorder, the recorder providing a channel for each detector of the array. Subsequently, the intensity variations produced as the recorded output may be analyzed first to determine the peak intensity of each detector for each cell to be analyzed, the peak intensities being combined to produce differential light scattering patterns such as shown in FIG. 4.

These patterns, or portions of these patterns, may be analyzed in any of various ways to identify, classify, and characterize the cells which produce them. For example, referring to FIG. 4b, the particles of identical size but of slightly different refractive indices corresponding to different protein compositions which produced the patterns presented in that figure may be distinguished from one another on the basis of the secondary peak amplitudes relative to the amplitude of the first peak, the first peak being that at approximately 25°. The table below lists these ratios for the first four peaks.

TABLE I

Figure 4A:
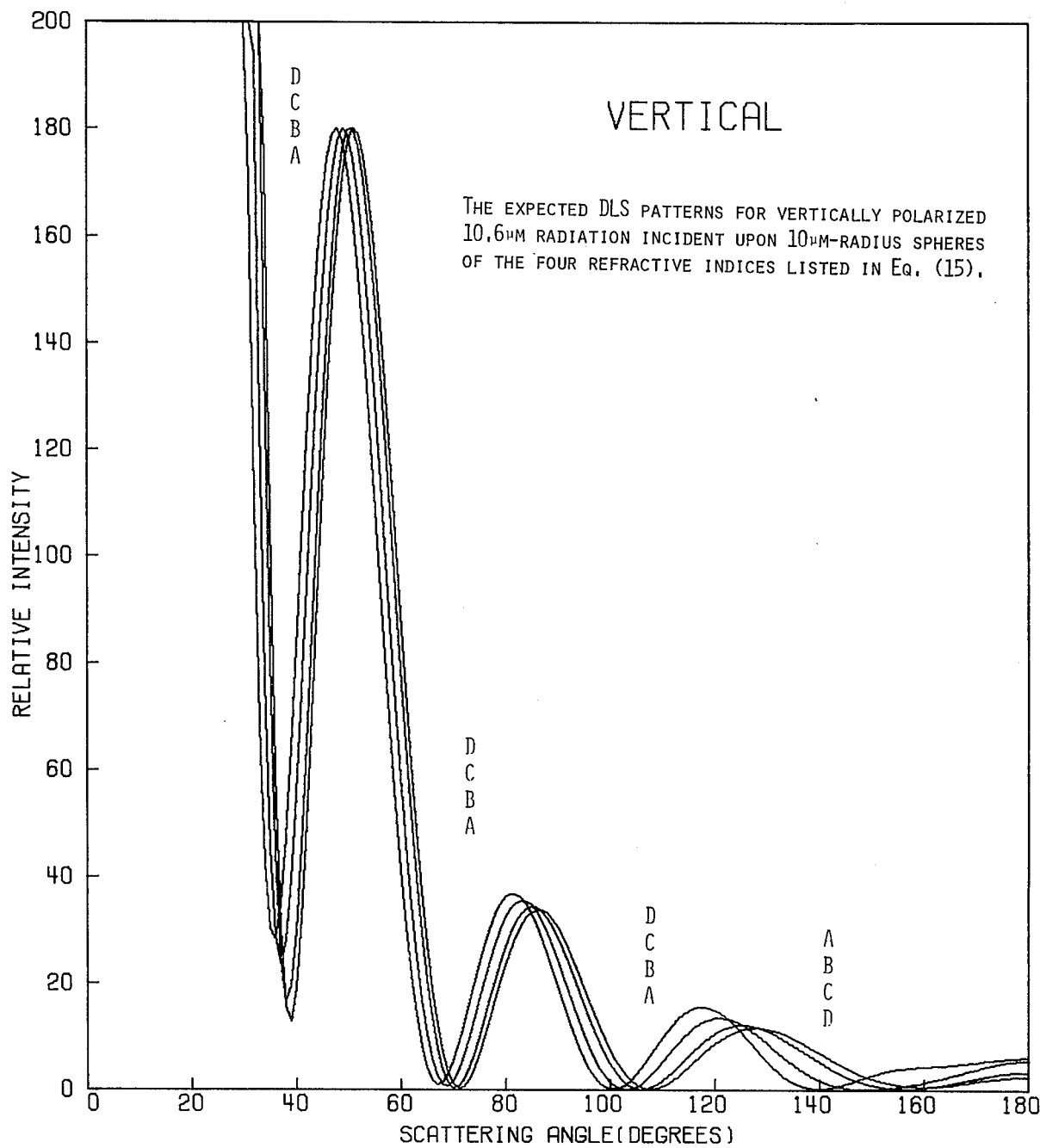
FIGS. 4 a–d present examples of some differential light scattering patterns in the infrared from particles with high water content.
Figure 4B:
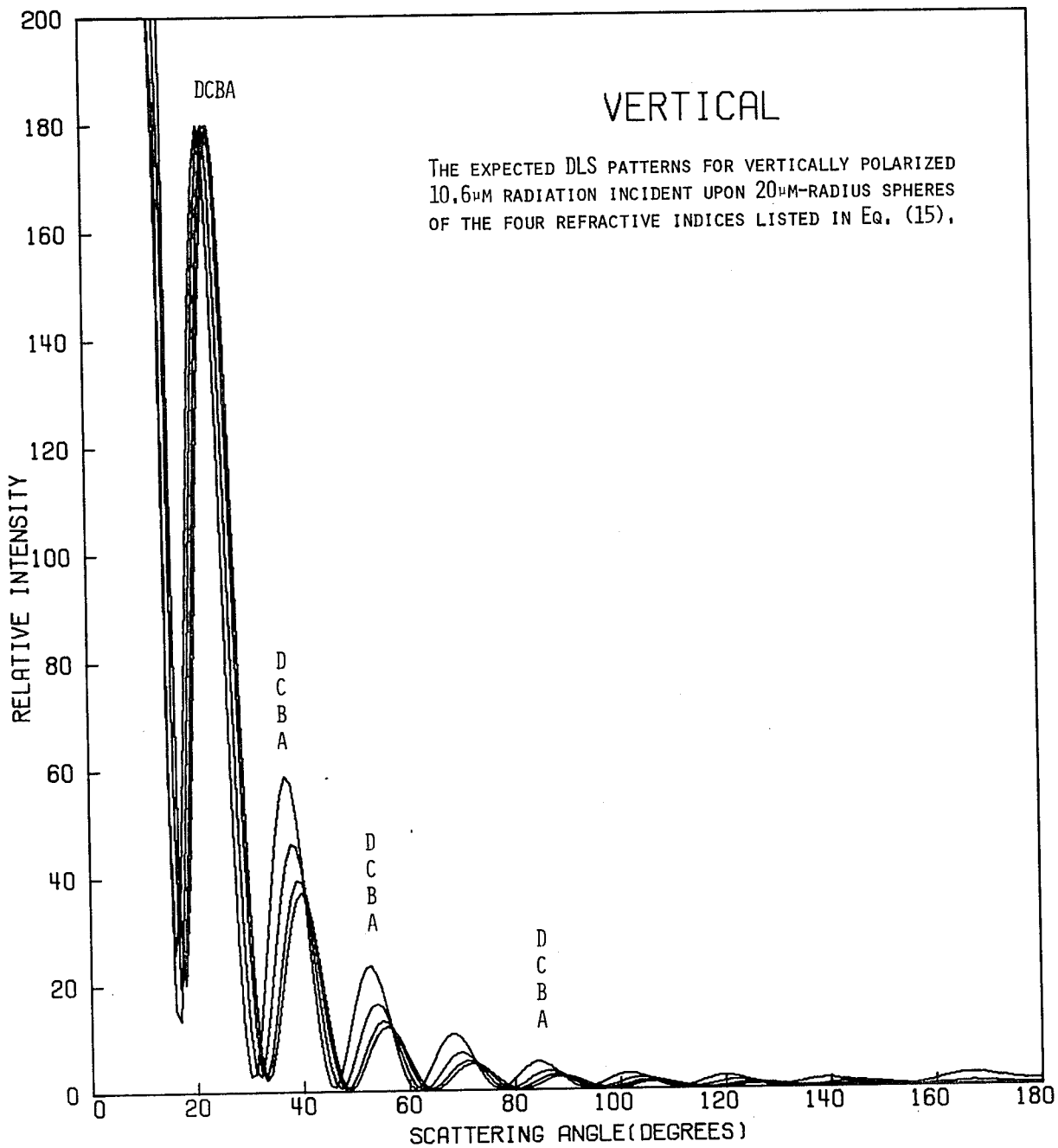
Figure 4C:
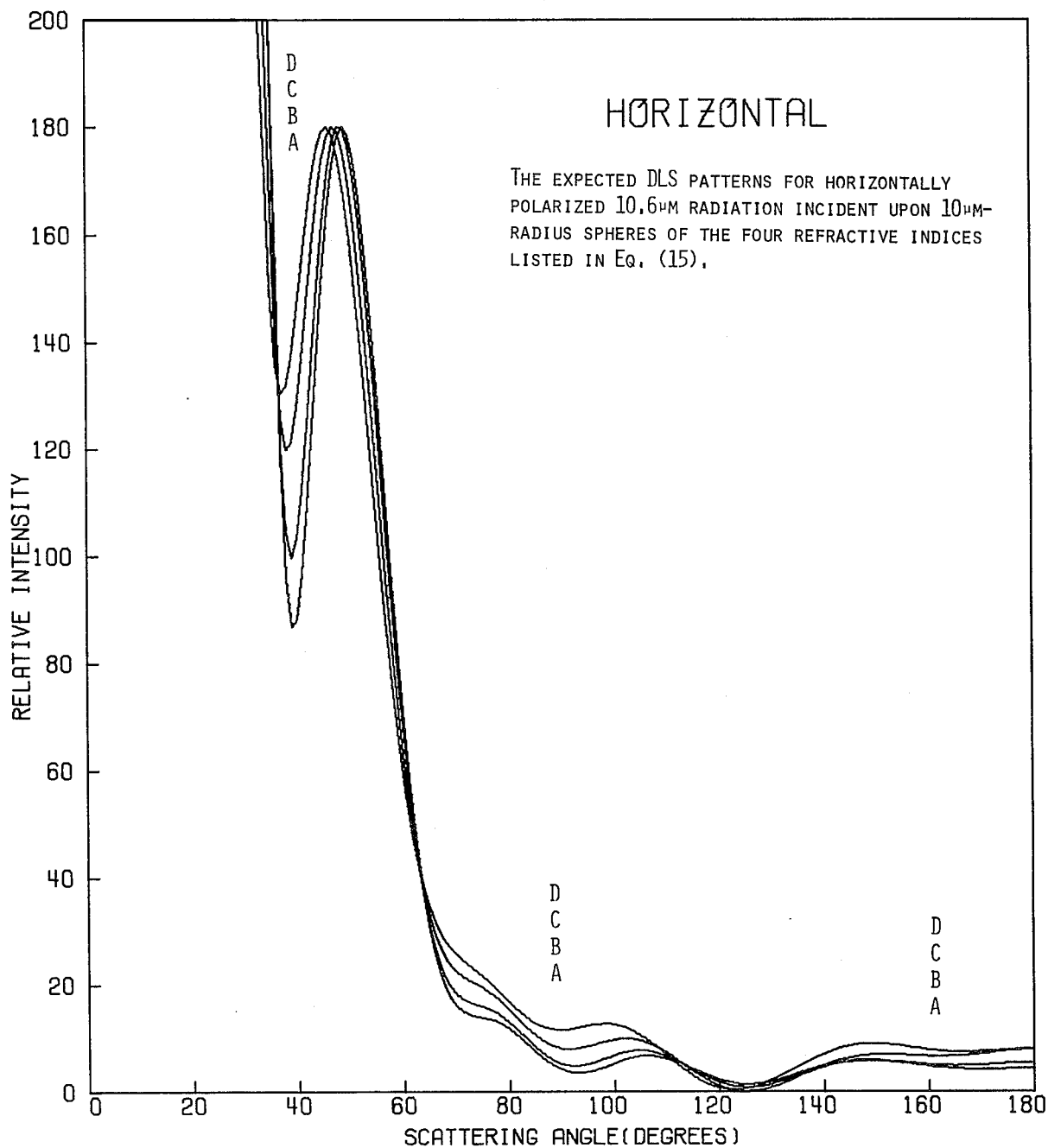
Figure 4D:
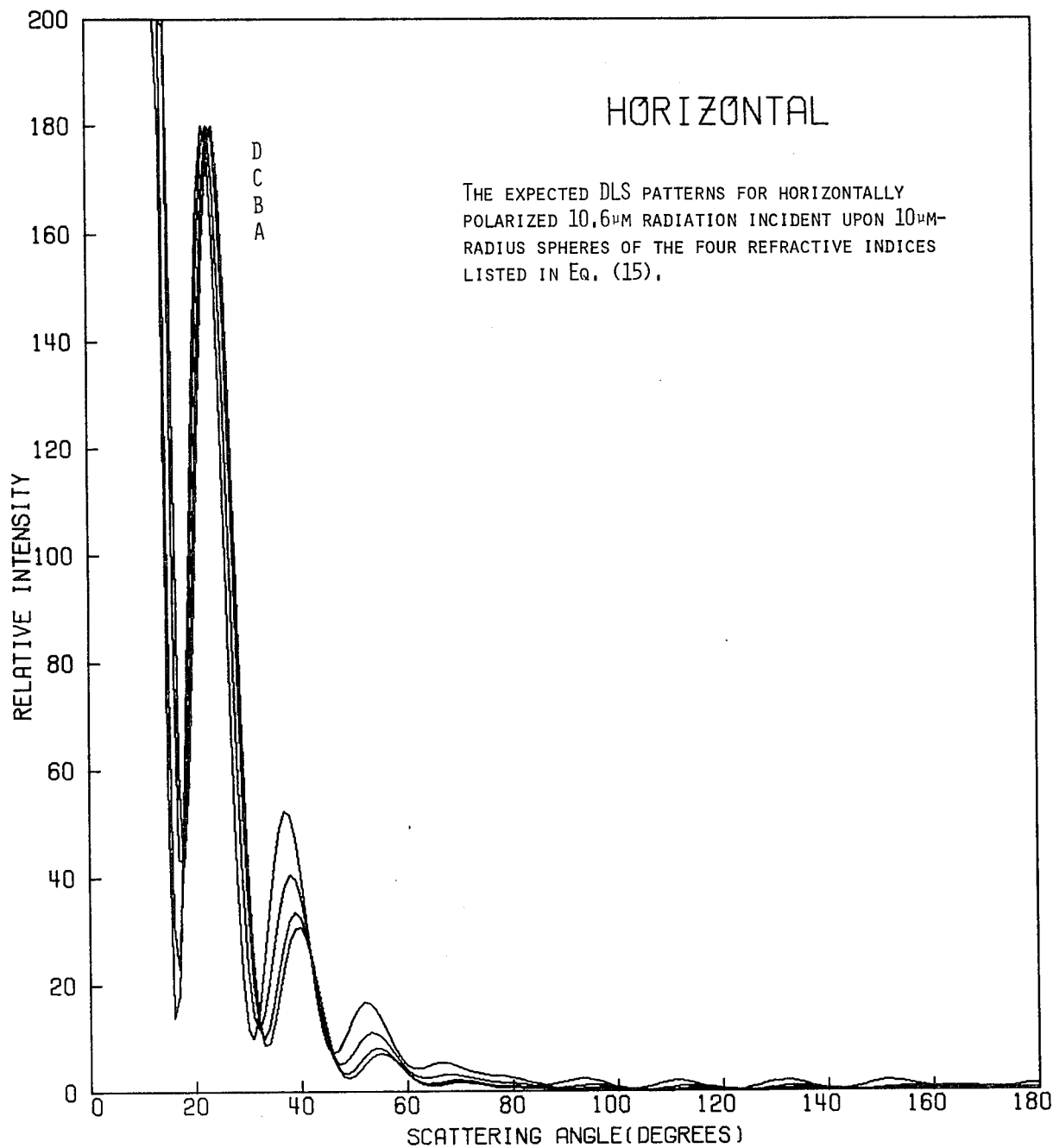

DLS PEAK RATIO FOR FIG. 4b

| Peak | PARTICLE | A | B | C | D |
|---|---|---|---|---|---|
| 1 | | 1 | 1 | 1 | 1 |
| 2 | | .33 | .30 | .21 | .19 |
| 3 | | .13 | .089 | .078 | .067 |
| 4 | | .056 | .033 | .026 | .022 |

As this table readily illustrates, based upon such different peak ratios, particles of the same size but of slightly different physical properties easily may be differentiated. Thus, to discriminate among particles of different size and different structure, such as are present in a suspension of the mammalian cells, the differential light scattering patterns which result from the various individual particles first may be separated by the number of peaks they present, this separation collecting into groups those light scattering patterns arising from particles of approximately the same size. After such a rough size grouping, those particles of approximately the same size may be compared with one another. As a first differentiation of these particles, the intensity of the first peak may be used as a standard value and the ratio of the second peak to this first peak intensity measured and employed as a more accurate differentiation than simply a size differentiation. Indeed, as has been noted, leucocytes include a number of different cell types, cell types which range in size from lymphocytes at approximately eight micrometers in size to granulocytes at approximately 18 micrometers. The size of appreciable numbers of these cells will be approximately the same, say in the order of 12 to 13 micrometers. Such particles may have approximately four to five peaks in their light scattering pattern when illuminated with vertically polarized monochromatic infrared radiation. If the ratio of the first to the second peak is employed to differentiate these particles in a simple, two-dimensional analysis, various overlapping Gaussian distributions will result generally in accordance with the overlapping distribution of leucocyte types in this smaller size range. To further differentiate these distributions, each successive peak ratio may be employed in a multi-dimensional vector analysis. While such an operation may be performed by hand, it is more convenient to employ a standard pattern recognition technique such as a typical multidimensional vector space partition analysis to group samples of similar characteristics using, for example, an appropriately programmed electronic computer.

Such an analytical approach is well within the ability of one skilled in the art and indeed today is performed routinely to classify complex data employing a multidimensional array.

When a large number of cells are to be analyzed, or for other reasons it is inconvenient to perform the cell identifcation and classification by hand as just described, an electronic system as shown in FIG. 5 may be employed. In this system, the output of each detector of the detector array 6 is supplied preferably to a logarithmic amplifier 72.

By converting each detector output signal which is a linear function of light intensity, produced at each detector, into a logarithmic value as achieved by a logarithmic amplifier 72, the dynamic range of the system is broadened considerably without increasing the digital data handling requirements. In addition, manipulating and comparing the data is simplified appreciably, since, for example, to determine ratios it is only necessary to subtract logarithms. On the other hand, with the rapid advent of inexpensive digital calculators, the alternative use of linear amplifiers supplemented by more complex arithemtic operations would be equally attractive. The response of these separate logarithmic or linear amplifiers may be standardized initially by causing light of a uniform intensity to strike all the detectors of the array simultaneously and then adjusting the amplifiers so that all produce the same output.

Detector standardization may not be required if the absolute differences between the gains of the individual detectors are measured and stored for subsequent arithmetic correction. Alternatively, any intensity set produced by a single particle could be used as a reference set by which all subsequent sets could be normalized or corrected.

Since the linearity of each detector of the infrared sensitive array discussed earlier is excellent, the outputs of the logrithmic amplifiers, by means of the standardization adjustment, will accurately represent the logarithm of the respective intensities of the illumination striking the respective detectors. These logarithmic amplifiers may be of the type made by Analog Devices, Inc., device no. 755. These respective outputs are transmitted to sample and peak detectors 74 such as manufactured by Burr Brown, device no. 4084.

A discriminator 76 is connected to the logarithmic amplifier supplying the output of the lowest angle detector. As the intensity produced by this low-angle detector varies in response to passage of the particle, the variation is noted by the discriminator. The discriminator 76 also is connected to the peak detectors 74 and holes them in a clear state until the previous analytical cycle is completed and the next cycle begins. This is triggered by the intensity of the output of the logarithmic amplifier connected to the lowest angle detector exceeding a predetermined level sufficient to indicate that a particle is passing through the beam of monocromatic radiation. As the particle passes through this beam, the output of each detector varies, reaching a maximum value which is stored by the peak detector 72 connected to it. These stored intensities correspond to the intensities of the differential light scattering pattern produced by that particle at the various successive angles of the detectors. As the source particle passes out of the laser beam, the intensity sensed by the lowest angle detector diminishes. The discriminator 76 responds to this decreasing magnitude and actuates a control logic system 78 by means of a connection 80. The control logic system 78 in turn actuates an analog to digital conversion device 82 which is sequentially connected by means of a multiplexer 34 to each peak detector 74. Such a multiplexer and conversion device may be, for example, that offered by Burr Brown as data acquisition unit MP 8126.

As a result of this processing, the logarithmic analog signal stored in each of the peak detectors is sensed and converted to a digital representation. This representation is transmitted to a memory system 86, preferably formed by emitter coupled logic components such as manufactured by Motorola, where it is stored in sequence with the other successive digital representations. Accordingly, stored in the memory unit is a digital representation of the peak value of the scattered light intensity sensed by each successive detector in array 44. After this operation, the control logic system 78 signals the discriminator 76 to permit new data to be accepted.

In the preferred embodiment, the memory unit 86 is connected to a microprocessor 88. The microprocessor examines the data by cycling through the digital information stored in the memory to determine the number of peaks present, employing mathematical interpolation if the number and spacing of the detectors are insufficient to provide the desired accuracy, this examination resulting in a digital sequence output representing the number, location, and values of such peaks. More specifically, the microprocessor analyzes the data to determine, for example, the ratio of the intensity of the second peak measured to the ratio of the intensity of the first peak measured, producing a first ratio, the digital representation of which is held by the microprocessor. In similar fashion, the microprocessor processes the data stored in the memory unit to determine the successive peak ratios, thereby resulting in a digital output that indicates, first, the number of peaks in the differential light scattering pattern produced by the particle just sensed by the detector array, then the peak ratios of this particle such as those ratios set forth in Table I.

The microprocessor 88 and the control logic system 78 both may utilize bipolar high-speed bitslice microprocessors such as those manufactured by Motorola or Texas Instruments, for example Motorola microprocessor no. MC10800. This microprocessor is controlled by a programmable read-only memory to perform the sequential analysis as just described or any other desired analysis.

The resulting stream of digital data may be recorded such as on a disc data storage unit 90, or it may be displayed on a video terminal 92, or complied as a hard copy output by printer 94, or it may be stored in a larger memory. While the storate unit, video terminal, and printer may be connected directly to the microprocessor, preferably further analysis of the data is performed by a minicomputer 96, the central processor of which first causes the data to be transmitted to the disc data storage unit 90. Then it analyzes the stored data by, for example, a multidimensional vector space partition analysis program or other suitable sorting algorithm as previously noted to construct a video display on terminal 92 of the various cell types present in the suspension supplied to the system, this display being printed in response to a user command by printer 94. The minicomputer 96 is a Digital Equipment Corporation PDP 11-20 unit, although various other computer systems will quite satisfactorily perform this analysis as is well known to those skilled in this art.

Many previous systems employing a detector or a detector array to measure the light scattered by an object over a substantial arc emphasize the importance of maintaining the detector or detector array at a constant radial distance from the object throughout the measurement arc. It is preferred to employ a detector array in the apparatus of this invention, as previously noted. This requirement of a constant radial distance imposes significant limitations upon the array. Not only must it be fabricated to form an arc of the appropriate radius and length, but also in accordance with prior teachings, the sensitivity of each element of the detector array should be quite uniform. Such limitations significantly increase the cost of the array and the cost of the associated electronics system required to achieve and maintain such uniformity.

The reason for this requirement is that light intensity diminishes inversely as the square of its distance from the scattering object. Thus, if a detector array is used, and all of the detectors in the array are not all exactly the same distance from a uniformly radiating object, unequal intensities will fall upon the elements of the array. Further, the surface area of the elements should be exactly equal so that they intercept the same solid angle of radiation, all to achieve a uniformity of response of each detector in the array to uniform scattering by the illuminated object. Only by realizing such uniformity will light scattering patterns such as illustrated in FIGS. 4 be achieved.

Figure 6A:
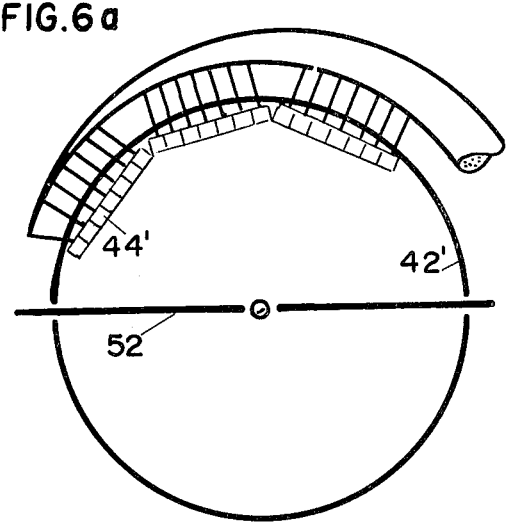
FIG. 6 a–c are sets of views similar to FIG. 3 of other versions of the detector array.
Figure 6B:
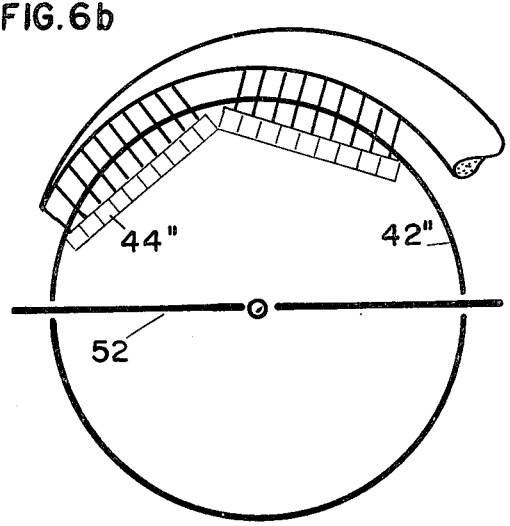
Figure 6C:
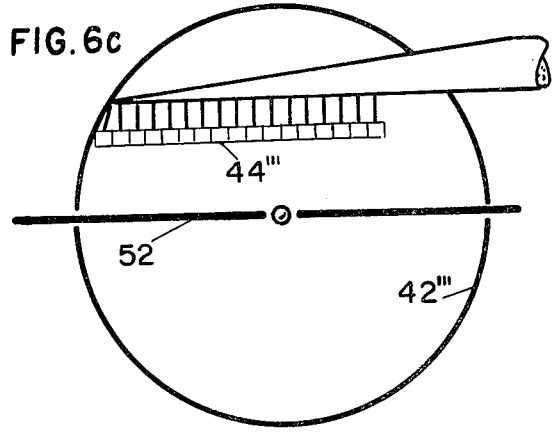

An important aspect of the present invention is the teaching that such uniformity need not be present in the detector array. Indeed, the detector array may consist of a number of linear segments deposed about the interior of the housing, the linear segments being configured as shown in FIGS. 6. Of course, a greater or lesser number of segments may be employed if desired, and they may be configured in various other manners. Each adjacent element or detector of the array, being at a different radial distance from the scattering object, will intercept light scattered in a different solid angle. In addition, these detectors need not be in the same plane. These differences and others in the array all will contribute to a significant distortion of the intensity of light sensed by the detectors constituting the array. This distortion can be considered to be a simple transformation of the undistorted scattering pattern. However, such a transformation need not result in erroneous characterizations of the analyzed cells. The light scattered by each substantially identical cell will result in a substantially identical, though transformed, differential scattering pattern being supplied to the processing system. Similarly, cells of different characteristics will result in correspondingly different scattering patterns similarly transformed and supplied to the processing system. For discrimination, characterization, or identification purposes, it is only necessary to achieve a consistency among the array elements and their responses transmitted to the processing system from identical particles illuminated in their transit through the detector housing, and a difference between the transformed scattering patterns applied to the preprocessor for substantially different cells being illuminated in the detector housing. Even though a detector array composed of various linear detector segments, as shown in FIGS. 6, results in a transformation of the true scattering pattern, the transformed pattern still results in substantially identical light scattering patterns being supplied to the preprocessor as the result of substantially identical cells being illuminated, and substantially different patterns being applied to the processing system for substantially different cells. Thus, the system is still capable of correlating substantially identical cells and distinguishing among non-identical cells. For this reason, significant savings in cost and simplification in structure of the detector array is realized in the disclosed apparatus while still attaining a major objective of the invention: rapid, unambiguous differentiation, characterization and identification of mammalian cells and other large particles such as pollens and fungal spores.

Figure 7:
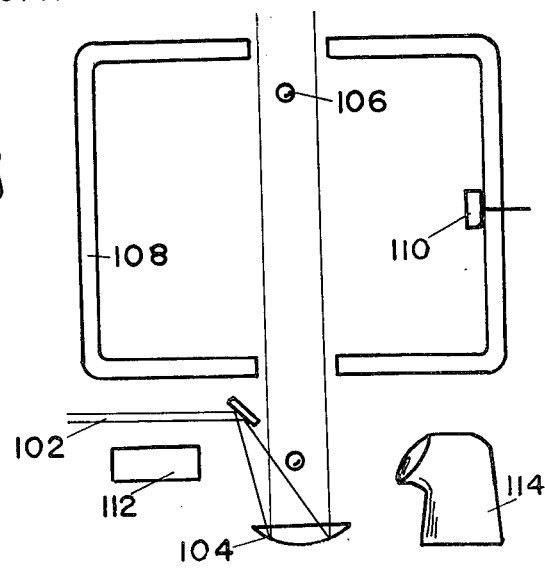
FIG. 7 is a view in vertical cross-section of another detector housing.

It should also be noted that the transformed DLS patterns that are measured for subsequent identification and discrimination of the source particles may be of many different types and measured in many different ways. Though desirable, even an array is not essential for this purpose as there are other alternatives for measuring and recording DLS patterns. If the source of illumination is co-linear with the particle stream, a single detector will synthesize the DLS pattern of a continuous array. Such an arrangement is illustrated in FIG. 7. A beam of illumination 102 is reflected from a mirror 104 shaped to direct the beam along the path of fall of the cells 106. As each cell passes into the detector housing 108, it comes into the field of view of the single detector or sensor 110. During the transit of the cell through the housing, its scattered illumination is viewed continuously by detector 110. Thus, the output of the detector will be a continuous representation of the illumination scattered by the cell from the lowest angle viewable by the detector as the cell passes into the housing to the highest angle viewable as the cell exits from the housing. This representation, when plotted as a function of time (and thus of scattering angle) will be the differential light scattering pattern of the cell and may be employed in the analytical system previously described. As the cell approaches mirror 104 it is deflected by an air jet 112 into a reservoir 114.

Another way to measure differential light scattering patterns employs a single, rotating detector. If a single detector may in effect be made to rotate about the particle in a period shorter than the particle's transit time through the perpendicular illuminating beam, a sufficient DLS pattern may be obtained. Such a configuration is described in an article by Marshall, Parmenter and Seaver, *Science*, Vol. 190, October, 1975, pgs. 375-377, "Precision Measurement of Particulates by Light Scattering at Optical Resonance", particularly with reference to FIG. 3. Alternatively, the particles may be electromagnetically captured and scanned individually as shown by Phillips, et al. in their U.S. Pat. No. 3,754,830.

For subsequent mathematical analysis, any such DLS pattern, or section thereof, may be converted to a digital representation. As discussed earlier and reemphasized here, any such pattern may be sufficiently characterized by N coefficients where N is approximately $\simeq 2\rho$, or alternatively by means of N discrete intensity values spanning the angular range of interest. For digital purposes it is probably most economical to store such DLS patterns in terms of the N coefficients, by which means they may be reconstructed later, than the much greater set of numbers corresponding to the digital storage of DLS patterns obtained from the synthetic continuous array derived from a single detector configuration of the types described above.

While a preferred system and components have been disclosed, depending upon the number of cells desired to be stored by the system per minute, slower and less expensive components may be employed, or faster components may be required. Of course, the cycle time of these components also is related to the number of detectors in the detector array. For the system disclosed, using a detector array of 10 to 50 sensors, a cell throughput rate may be achieved on the order of 1,000 to 60,000 cells per minute, a rate more than adequate to equal or exceed most cell sorting requirements. In addition to using faster components, higher sorting rates also may be achieved by using multiple memories and micro-processing systems, since in the stream of cells the average cell rate will be appreciably less than the maximum cell rate due to the fact that a number of droplets will contain no cells and will be deflected from the cell stream by the cell sorter.

While preferred embodiments of the invention have been disclosed and described, as previously noted, various other embodiments may be preferred by others skilled in this art. Accordingly, the scope of the invention is not limited to the preferred embodiment.

What is claimed:

1. A process for analyzing the cells of a size substantially larger than a wavelength of visible light, the cells being in a liquid suspension, the process comprising the steps of:
   Aerosolizing the suspension of cells to produce a series of droplets, some of which contain a cell;
   Separating those droplets containing a cell from the other droplets which do not contain cells;
   Illuminating in sequence the separated cells with a beam of monochromatic radiation of a wavelength which, when compared to the size of the cell, is in the resonance region;
   Detecting radiation intensities of a given polarization scattered by each illuminated cell to obtain a differential scattering pattern characterizing the size, shape, and dielectric properties of each cell; and Recording the detected patterns to characterize the illuminated cells.

2. A process for analyzing cells as set forth in claim 1 in which the detected intensities are analyzed by:

Determining the extrema within the set of intensities detected for each pattern;

Counting the number of extrema within the set of intensities detected to produce a total count for each pattern;

Associating such total count with an average size interval; and

Comparing each detected pattern with a set of reference patterns of the associated average size interval to characterize or associate each particle with a known reference pattern by this comparison.

3. A process for analyzing cells as set forth in claim 1 in which the radiation employed to illuminate the cells is of a wavelength that is no greater than substantially equal to the size of the cells and no less than approximately one twentieth the size of the cells.

4. A process for analyzing cells as set forth in claim 3 in which the detected patterns are analyzed by Locating the angular locations of the extrema of the pattern represented by the angular sequence of detected signals for each cell to obtain sets of extrema data, one set for each cell;

Grouping the sets of extrema data into particle size groups based on the number of extrema in a selected angular range;

Normalizing each extrema intensity value relative to the intensity value of a reference extrema value; and Comparing such normalized values with a reference set of values to associate each analyzed cell with one of a reference set of cells.

5. A process for analyzing cells as set forth in claim 4 in which the reference set of values are obtained by analyzing a suspension of known cells by a process comprising the steps of:

Aerosolizing the suspension of cells to produce a series of droplets, some of which contain a cell;

Separating those droplets containing a cell from the other droplets which do not contain cells;

Illuminating in sequence the separated cells with a beam of monochromatic radiation of a wavelength which, when compared to the size of the cell, is in the resonance region;

Detecting radiation intensities of a given polarization scattered by each illuminated cell to obtain a differential scattering pattern characterizing the size, shape, and dielectric properties of the cell; and Recording the detected patterns to characterize the illuminated cells.

6. A process for analyzing cells as set forth in claim 5 including the step of:

Evaporating the liquid surrounding each cell droplet prior to illuminating in sequence the separated cells.

7. A process for analyzing cells as set forth in claim 6 in which the cells are organic cells from the group consisting of mammalian cells, fungal spores, and pollen.

8. A process for analyzing cells as set forth in claim 5 in which the radiation intensities are detected by elements of a detector array at a sufficient number of angular locations relative to the direction of the illuminating beam to derive a pattern representative of a differential scattering pattern.

9. A process for analyzing cells as set forth in claim 8 where the number of locations $N \simeq [2\pi D_{max} n_o/\lambda_o + 4]\theta/\sim°$ where:

$\theta$ is the angular range in degrees spanned by the detectors;

$n_o$ is the refractive index of the medium in which the measurement is made;

$D_{max}$ is the largest cell or particle diameter of the ensemble being examined; and $\lambda_o$ is the vacuum wavelength of the incident radiation.

10. A process for analyzing cells as set forth in claim 9 in which the angular locations of the N detectors of the detector array are given by the N roots of the Tchebychev polynomial $T_N(X)$ where:

$$X = \frac{\theta - (\theta_1 + \theta_2)/2}{(\theta_2 - \theta_1)/2},$$

and $\theta_1 < \theta_2$ are the two limiting angles defining the angular range of the pattern to be measured.

11. A process for analyzing cells as set forth in claim 5 in which the reference set of values are obtained by examining each droplet in the suspension of known cells to detect the presence of a cell in it prior to the separating step.

12. A process for analyzing cells as set forth in claim 1 in which each droplet is examined to detect the presence of a cell in it prior to the separating step.

13. An apparatus for analyzing cells of a size substantially larger than a wavelength of visible light, the cells being in a liquid suspension including:

Means for aerosolizing the suspension of cells to produce a stream of droplets, some of which include a cell;

Means to separate those droplets in the suspension which include cells from the other droplets which do not include cells;

Means individually illuminating the separate cells with a beam of monochromatic radiation, the radiation being of a wavelength which, when compared to the size of the illuminated cell, produces resonant scattering;

Means detecting the intensities of a given polarization scattered by the illuminated cell to obtain a differential scattering pattern characterizing the size, shape, and dielectric properties of the cell; and Recording the detected pattern for each illuminated cell to thereby characterize each cell.

14. An apparatus as set forth in claim 13 in which the radiation intensities are detected by elements of a detector array at a sufficient number of angular locations relative to the direction of the illuminating beam to derive a pattern representative of a differential scattering pattern.

15. An apparatus as set forth in claim 14 in which the number of locations $N \simeq [2\pi D_{max} \; n_o/\lambda_o + \alpha]\theta/\frac{1}{2}°$ where:

$\theta$ is the angular range in degrees spanned by the detectors;

$D_{max}$ is the largest cell or particle diameter of the ensemble being examined; and $n_o$ is the refractive index of the medium in which the measurement is made.

$\lambda_o$ is the vacuum wavelength of the incident radiation.

16. An apparatus as set forth in claim 15 in which the spacing of the N detectors of the detector array are given by the N roots of the Tchebychev polynomial $T_N(X)$ where:

$$X = \frac{\theta - (\theta_1 + \theta_1)/2}{(\theta_2 - \theta_2)/2},$$

and $\theta_1 < \theta_2$ are the two limiting angles defining the angular range of the pattern to be measured.

17. An apparatus as set forth in claim 14 including:

A detector housing;

Means detecting the scattered intensities comprising an array of detectors deposed about the interior of the housing; and Means directing aerosolized cells individually through the detector housing, the illuminating beam passing through the detector housing and illuminating the individual cells during their transit through the housing.

18. An apparatus of claim 17 in which the detectors are not equally spaced in angle.

19. An apparatus of claim 18 in which the spacing of the N detectors of the detector array are given by the N roots of the Tchebychev polynomial $T_N(X)$ where $$X = \frac{\theta - (\theta_1 + \theta_2)/2}{(\theta_2 - \theta_1)/2},$$

and $\theta_1 < \theta_2$ are the two limiting angles defining the angular range of the pattern to be measured.

20. An apparatus as set forth in claim 17 in which the individual detectors of the detector array are at different radial distances from the point at which a cell in the housing is illuminated by the beam.

21. An apparatus as set forth in claim 20 in which the detectors in the array view radiation along axes deposed in a single plane, this plane including the axis of the illuminating beam.

22. An apparatus as set forth in claim 21 in which the linear detector array consists of at least one set of planar detector elements all being deposed in substantially the same plane.

23. An apparatus as set forth in claim 13 in which the wavelength of the illuminating beam is no greater than substantially equal to the size of the illuminated cells and no less than substantially one twentieth the size of the illuminated cells.

24. An apparatus as set forth in claim 13 including means for analyzing the set of intensities detected comprising:
Means determining the extrema within the set of intensities detected for each pattern;
Means counting the number of extrema within the set of intensities detected to produce a total count for each pattern;
Means associating such total count with an average size interval; and
Means comparing each detected pattern with a set of reference patterns of the associated average size interval to characterize or associate each particle with a known reference pattern by this comparison.

25. An apparatus as set forth in claim 24 including:

Means comparing each of the extrema values in the extrema set to an associated reference extrema value to yield a set of normalized data; and Means comparing the detected and reference patterns comparing normalized data.

26. An apparatus as set forth in claim 25 including:
A detector housing;

Means detecting the scattered intensities comprising an array of detectors deposed about the interior of the housing; and Means directing aerosolized cells individually through the detector housing, the illuminating beam passing through the detector housing and illuminating the individual cells during their transit through the housing.

27. An apparatus as set forth in claim 26 in which the detectors in the array view radiation along axes deposed in a single plane, this plane including the axis of the illuminating beam.

28. An apparatus as set forth in claim 27 in which the detectors of the array are generally planar in shape, the detectors being located at offset irregular positions about the illuminated cell and at substantially different radial distances from said cell, at least some of the detectors being coplanar with the incident radiation beam.

29. An apparatus as set forth in claim 13 including means to examine each droplet in the aerosolized suspension to detect the presence of a cell in it prior to separation of the droplets.

30. An improved detector system for a photometer, the photometer including an illuminating beam, means for locating the sample in the illuminating beam to produce radiation scattered by the sample, the improved detector system including means locating the detector generally along a linear path to measure the scattered intensity at offset angular locations about said sample, said means locating the detector to measure the scattered intensity at substantially different radial distances from said sample location, the detector locations at lower acute scattering angles being at substantially greater radial distances from said sample location than the detector locations at higher acute scattering angles.

31. An improved detector system as set forth in claim 30 in which the detector comprises an array of detector elements, different elements producing substantially different electrical responses to scattered radiation, individual detector elements being located to measure the scattered intensity at offset angular locations about said sample location and at substantially different radial distances from said sample location.

32. An improved detector system array as set forth in claim 31 including a series of discrete detectors, the detectors being aligned to view along axes all in a plane, which includes the axis of the illuminating beam.

33. An improved detector system array as set forth in claim 32 in which the discrete detectors are generally planar in shape, at least some of the detectors being aligned in the same plane.

* * * * *